Figure 1:
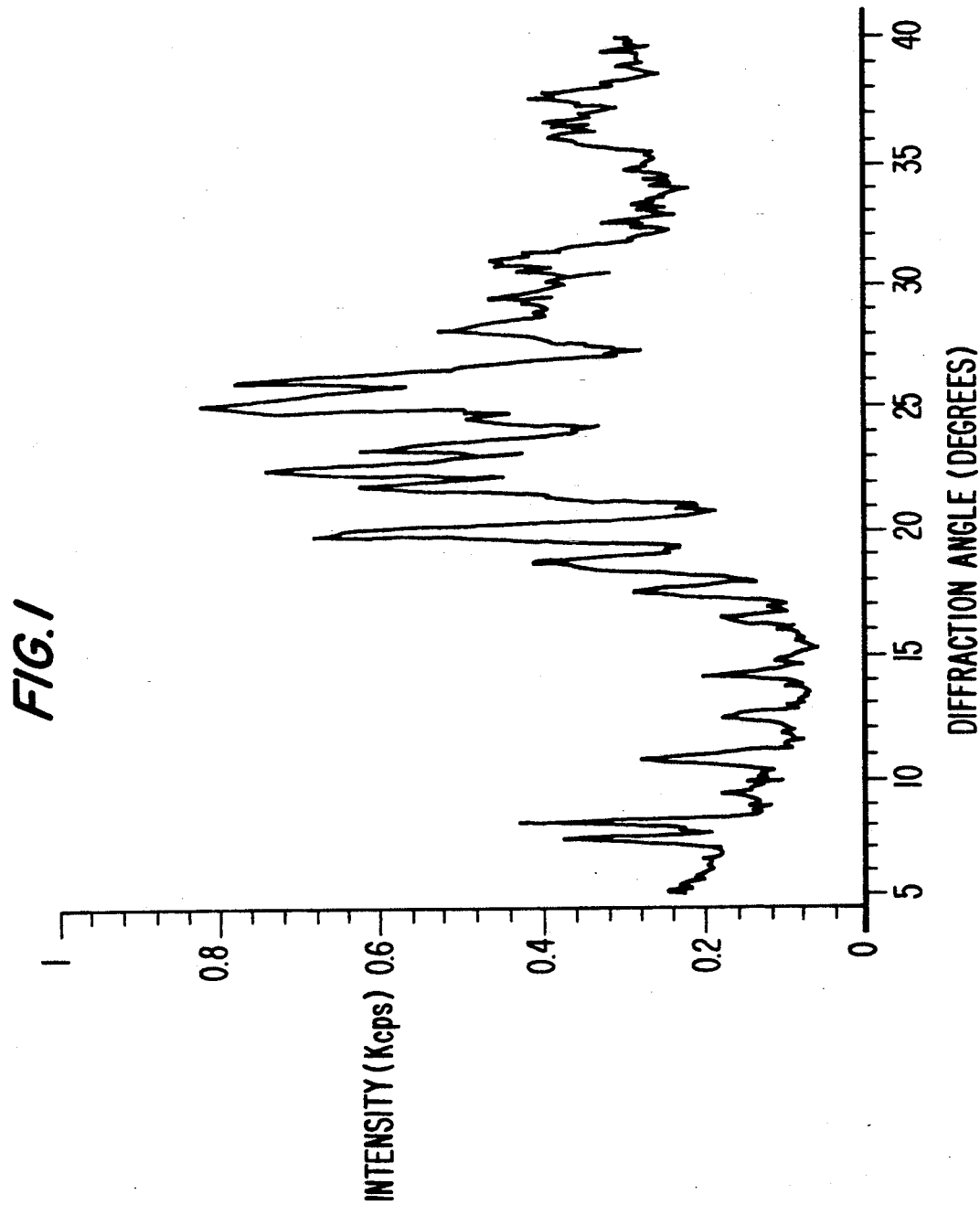

United States Patent [19]

Ikai et al.

[11] Patent Number: 5,162,581

[45] Date of Patent: Nov. 10, 1992

[54] CRYSTALLINE DEOXYSPERGUALIN, PROCESS FOR ITS PREPARATION AND SUPPOSITORY CONTAINING THE SAME

[75] Inventors: Katsushige Ikai, Shiga; Makoto Moriguchi, Jyoyo; Yoshihisa Umeda, Otsu; Ikunoshin Kato, Uji; Tetsushi Saino, Yono; Hironobu Hiraga; Takaaki Ohkuma, both of Yono, all of Japan

[73] Assignees: Takaru Shuzo Co., Ltd., Kyoto; Nippon Kayaku Kabushiki Kaisha, Tokyo, both of Japan

[21] Appl. No.: 744,828

[22] Filed: Jul. 29, 1991

Related U.S. Application Data

[63] Continuation-in-part of Ser. No. 528,197, May 24, 1990, abandoned.

[30] Foreign Application Priority Data

May 29, 1989 [JP] Japan ............................ 1-132879
May 24, 1990 [JP] Japan ............................ 1-132878
Aug. 10, 1990 [JP] Japan ............................ 2-213505

[51] Int. Cl.$^5$ .......................................... C07C 237/02
[52] U.S. Cl. ..................................................... 564/157
[58] Field of Search ........................................ 564/157

[56] References Cited

U.S. PATENT DOCUMENTS

| | | | |
|---|---|---|---|
| 3,799,988 | 3/1974 | Hashimoto et al. | 564/159 |
| 4,416,899 | 11/1983 | Umezawa et al. | 514/616 |
| 4,430,346 | 2/1984 | Umezawa et al. | 564/159 |
| 4,518,532 | 5/1985 | Umezawa et al. | 564/157 |
| 4,556,735 | 12/1985 | Umezawa et al. | 564/157 |
| 4,983,328 | 1/1991 | Umezawa et al. | 564/157 |
| 4,990,538 | 2/1991 | Sakasai et al. | 564/157 |

Primary Examiner—James H. Reamer
Attorney, Agent, or Firm—Wenderoth, Lind & Ponack

[57] ABSTRACT

The invention provides crystalline deoxyspergualin trihydrochloride, a process for the preparation of the same and a suppository composition containing the same. The compound and composition has antitumor and immunosuppressive activity.

5 Claims, 5 Drawing Sheets

CRYSTALLINE DEOXYSPERGUALIN, PROCESS FOR ITS PREPARATION AND SUPPOSITORY CONTAINING THE SAME

This application is a continuation-in-part of now abandoned application Ser. No. 07/528,197 filed May 24, 1990.

This invention relates to crystals of N-[4-(3-aminopropyl)aminobutyl]-2-(7-guanidinoheptanamide)-2-hydroxy-ethanamide trihydrochloride (hereinafter referred to as deoxyspergualin hydrochloride), which has antitumor activity and immunosuppressive activity, a process for the preparation of the same and a suppository containing the same.

Deoxyspergualin, of the formula:

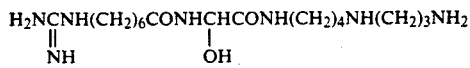

has excellent antitumor activity against various animal tumors and excellent immunosuppressive activity, and therefore it is a useful compound for clinical use. Deoxyspergualin has conventionally been prepared as the trihydrochloride salt.

For the preparation of deoxyspergualin hydrochloride, a synthetic method using the acid-catalyzed dehydration condensation of 7-guanidinoheptanamide with glyoxylylspermidine is known [U.S. Pat. Nos. 4,518,532 and 4,603,015].

The powder of deoxyspergualin hydrochloride obtained by the above-mentioned synthetic method has undesirable properties such as hygroscopicity and heat instability. This invention is to provide crystals of deoxyspergualin hydrochloride to improve the hygroscopic and heat-unstable properties of deoxyspergualin hydrochloride.

Briefly, the present invention relates to crystals of deoxyspergualin hydrochloride. The present invention also relates to a process for the preparation of crystals of deoxyspergualin hydrochloride, and the process is characterized by crystallizing a powder or water-suspension syrup of deoxyspergualin hydrochloride in the presence of water and a water-miscible or water-soluble organic solvent.

We have found for the first time that deoxyspergualin hydrochloride can be crystallized, and that the crystals have remarkably improved hygroscopicity, handling properties and heat stability as compared with the powder or lyophilized powder which has been conventionally prepared and used. This invention is based on such finding.

In this invention, the term "powder of deoxyspergualin hydrochloride" means the powder obtained from a water suspension syrup of deoxyspergualin hydrochloride by drying under reduced pressure, or the lyophilized powder. The term "water suspension syrup of deoxyspergualin hydrochloride" means a syrupy residue obtained by concentrating an aqueous solution of deoxyspergualin hydrochloride under reduced pressure. Usually the content of water in such syrup is 30% or less.

The crystalline deoxyspergualin hydrochloride of this invention has improved hygroscopicity and heat stability, and the crystals are in α-form or β-form.

α-form crystals of deoxyspergualin hydrochloride can be prepared in the following manner:

Deoxyspergualin hydrochloride itself can be prepared by various methods, and one of the methods is described in Example 4 of U.S. Pat. No. 4,518,532. The present invention is not limited to any particular method for the preparation of deoxyspergualin hydrochloride.

When the powder of deoxyspergualin hydrochloride is left standing in a low humidity atmosphere, preferably at a relative humidity (hereafter referred to as RH) of 52% or below, and at a suitable temperature, the powder is crystallized to the α-form crystals of deoxyspergualin hydrochloride of this invention.

The temperature used for the crystallization is not limited to any particular temperature or range of temperatures, provided that the temperature does not cause the degradation of deoxyspergualin hydrochloride. The temperature for practical use is in the range of 0° C. to 30° C. The time required for the crystallization is in the range of 2 to 20 days, and is usually about 10 days, depending upon the amount of the powder and humidity.

The α-form crystals can also be obtained from a syrup of deoxyspergualin hydrochloride. Thus, an aqueous solution of deoxyspergualin hydrochloride is concentrated to yield a syrup, which is then left standing in a low humidity atmosphere, preferably at a RH of 52% or below to give α-form crystals. The temperature and the time for crystallization may be similar to those mentioned above, but the time may be shortened by stirring the syrup during the crystallization or by adding a suitable amount of α-form crystals into the syrup.

The most practical process for the preparation of α-form crystals is as follows. To a water suspension syrup with a water content of 20% (w/w) or below is added a small amount of α-form crystals prepared in advance, and the syrup is stirred at a RH of 30% or less until it solidifies in a few hours. The crystallization becomes complete when stored in a silica gel desiccator.

The physicochemical properties of α-form crystals of deoxyspergualin hydrochloride are as follows.

1. X-ray Diffraction Pattern

An X-ray diffraction apparatus (Shimadzu XD-610) equipped with a Cu X-ray tube, graphite monochrometer and, scintillation counter for detection was used to study the X-ray diffraction pattern, which is shown in FIG. 1 and Table 1.

In FIG. 1 is shown the X-ray powder diffraction pattern of α-form crystals of deoxyspergualin hydrochloride with the diffraction angle (degrees) on the abscissa, and the intensity (Kcps) on the ordinate.

TABLE 1

| X-ray diffraction pattern of α-form crystals | | | |
|---|---|---|---|
| d (Å) | I/I₁ | d (Å) | I/I₁ |
| 11.78 | 0.46 | 4.04 | 0.76 |
| 10.64 | 0.53 | 3.90 | 0.91 |
| 7.49 | 0.34 | 3.78 | 0.76 |
| 5.03 | 0.36 | 3.50 | 1.00 |
| 4.72 | 0.51 | 3.39 | 0.95 |
| 4.39 | 0.84 | 3.12 | 0.64 |

X-ray source: Cu X-ray tube. 40 KV, 30 mA. λ = 1.54051
Filter: Graphite monochrometer

2. Thermoanalysis

Figure 2:
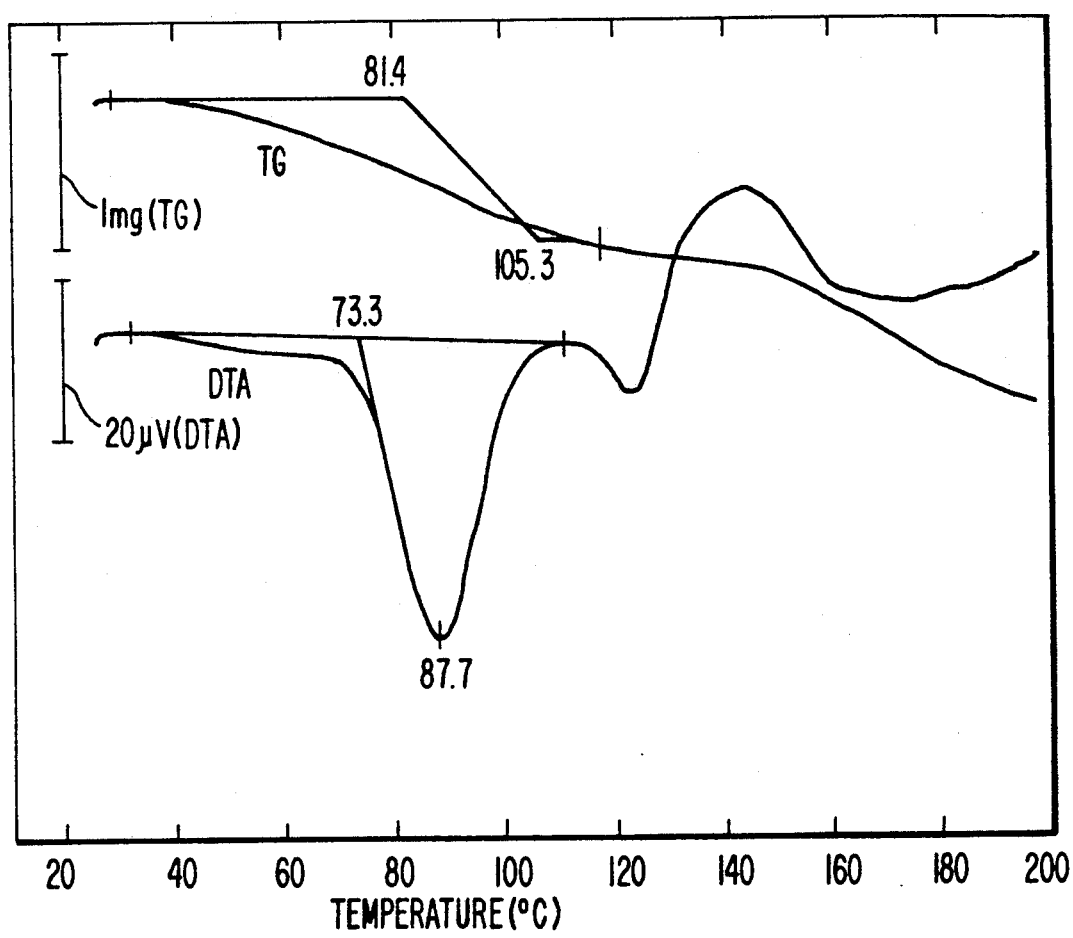

Results of differential thermal analysis (DTA) and thermogravimetry (TG), which were obtained simultaneously by using Rigaku Denki (Model TAS-100), are shown in FIG. 2 for α-form crystals of deoxyspergualin hydrochloride. Results are depicted with temperature (°C.) on the abscissa and weight (mg) or electron volts (μV) on the ordinate.

3. Hygroscopicity

To evaluate the hygroscopicity of the powder and α-form crystals of deoxyspergualin hydrochloride, the change of the weight of each sample was measured after storage in different RH (%) for 24 hrs. The results are shown in Table 2.

TABLE 2

Changes in weight under conditions of different humidity

| RH (%) | Increase in weight (%) | |
|---|---|---|
| | Powder | α-form crystals |
| 14 | 1.5 | — |
| 31 | 5.9 | −0.8 |
| 43 | 9.1 | −0.4 |
| 52 | 12.6 | −0.2 |
| 64 | 17.9 | 17.8 |

As shown in Table 2, the α-form crystals of deoxyspergualin hydrochloride did not absorb water at RH of 52% or below, showing improvement in hygroscopity as compared with powder.

4. Heat Stability

To evaluate the heat stability of α-form crystals of deoxyspergualin hydrochloride in comparison with that of the powder, samples were stored at 50° C. for 6 days and were analyzed by high-pressure liquid chromatography (HPLC), and the amount of undecomposed substance was measured. The results are shown in Table 3.

TABLE 3

| Comparison of heat stability | | |
|---|---|---|
| | Powder | α-form crystals |
| Amount (%) | 83 | 100.0 |

Note:
$\text{Amount (\%)} = \frac{\text{Amount after storage}}{\text{Initial amount}} \times 100$ As shown in Table 3, the α-form crystals show remarkable improvement in heat stability.

β-form crystals of deoxyspergualin hydrochloride can be prepared in the following manner. Deoxyspergualin hydrochloride itself can be prepared by various methods, and one of the methods is described in Example 4 of U.S. Pat. No. 4,518,532. The present invention is not limited to any particular method for the preparation of deoxyspergualin hydrochloride. When the powder of deoxyspergualin hydrochloride thus obtained is left standing in a mixture of water and a water-soluble or miscible organic solvent there are obtained β-form crystals of deoxyspergualin hydrochloride.

Organic solvents which may used for the crystallization in this invention are those which can be mixed with water to homogeneity. For example, methanol, ethanol, i-propanol, n-propanol, acetone, tetrahydrofuran, 1,4-dioxane, and a mixture thereof may be used. The most preferred solvent is ethanol, but there is no particular restriction thereto. The concentration of the solvent, e.g. ethanol in the solution to be used for the crystallization is usually in the range of 85 to 99.5% (v/v), and preferably in the range of 90 to 98% (v/v).

The temperature for the crystallization is not critical, provided that the temperature does not cause the degradation of deoxyspergualin hydrochloride, and usually it is in the range of −20° to 50° C., and preferably from 5° C. to room temperature. Time needed for the crystallization is in the range of 2 to 20 days, depending upon the amount of the hydrochloride used and usually, it is about 10 days. At the early stage of the crystallization, seeding a small portion of β-form crystals obtained in advance may promote crystallization.

In the above method, a syrup (water suspension syrup) of deoxyspergualin hydrochloride may be used in place of powder of deoxyspergualin hydrochloride. In this case the amount of water contained in the syrup should be taken into consideration so that the concentration of the organic solvent e.g. ethanol in the crystallization system is 85–99.5%, preferably 90–98% (v/v).

The proportion of the organic solvent used for crystallization to deoxyspergualin hydrochloride is not restricted, but is usually in the range of ratios of 3:1 to 20:1 (v/w).

Stirring during the crystallization reduces the time for crystallization; This time is in the range of a few hours to several days. β-form crystals thus formed can be collected by any ordinary method such as filtration under reduced pressure or filtration which makes use of centrifugal force.

The physicochemical properties of β-form crystals of deoxyspergualin hydrochloride are as follows.

1. X-ray Diffraction Pattern

Figure 3:
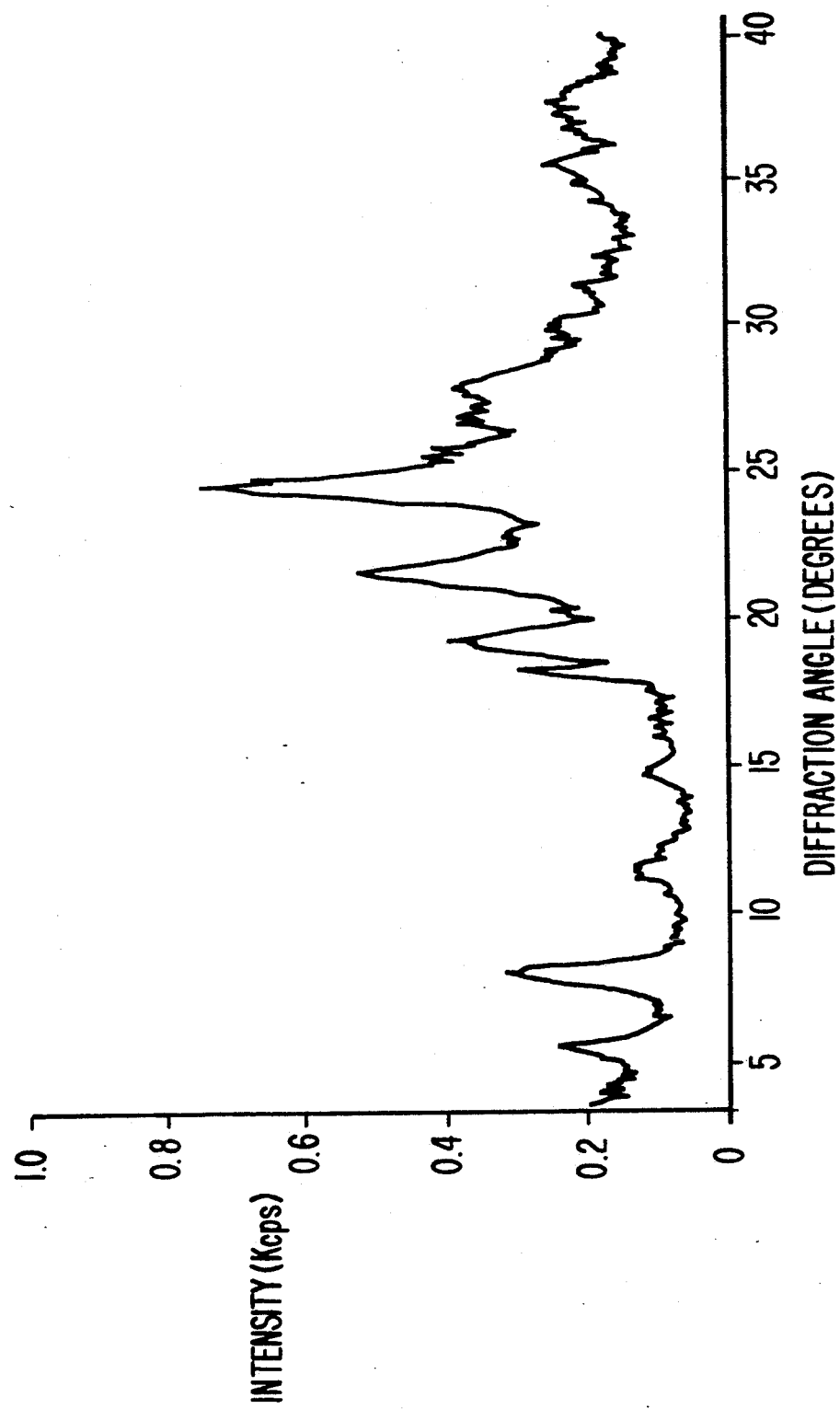

An X-ray diffraction apparatus (Shimadzu XD-3A) equipped with a Cu X-ray tube, graphite monochrometer and scintillation counter for detection was used to study the X-ray diffraction pattern, which is shown in FIG. 3 and Table 4.

In FIG. 3 is shown the X-ray powder diffraction pattern of β-form crystals of deoxyspergualin hydrochloride with the diffraction angle (degrees) on the abscissa, and the intensity (Kcps) on the ordinate.

TABLE 4

| X-ray diffraction pattern of β-form crystals | | | |
|---|---|---|---|
| d (Å) | I/I₁ | d (Å) | I/I₁ |
| 15.77 | 0.32 | 4.14 | 0.70 |
| 10.91 | 0.42 | 3.66 | 1.00 |
| 4.88 | 0.39 | 3.31 | 0.52 |
| 4.67 | 0.53 | 3.21 | 0.52 |

X-ray source: Cu X-ray tube. 40 KV, 30 mA. λ = 1.54051
Filter: Graphite monochrometer

2. Thermoanalysis

Figure 4:
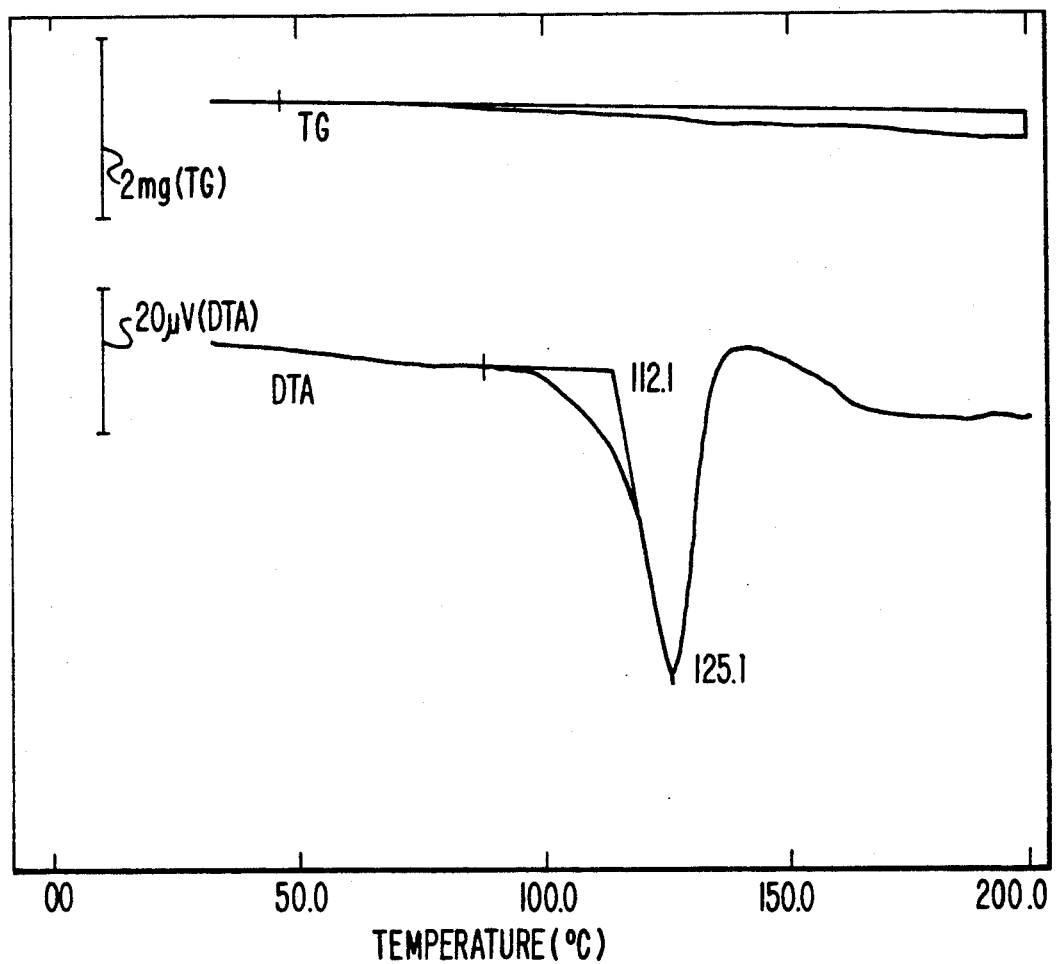

Results of differential thermal analysis (DTA) and thermogravimetry (TG), which were obtained simultaneously by using Shimadzu apparatus (model DTG-40) are shown in FIG. 4 for β-form crystals of deoxyspergualin hydrochloride. Results are depicted with temperature (°C.) on the abscissa and weight (mg) or electron volts (μV) on the ordinate.

3. Hygroscopicity

To evaluate the hygroscopicity of the powder and β-form crystals of deoxyspergualin hydrochloride, the change in the weight of each sample was measured after storage in different RH (%) for 24 hrs. The results are shown in Table 5.

TABLE 5

| | Changes in weight under conditions of different humidity | |
|---|---|---|
| | Increase in weight (%) | |
| RH (%) | Powder | β-form crystals |
| 31 | 5.9 | 1.7 |
| 43 | 9.1 | 2.6 |
| 52 | 12.6 | 3.8 |
| 64 | 17.9 | 7.3 |
| 76 | 28.3 | 14.0 |

As shown in Table 5, the change in the weight of the β-form crystals was less at all humidities than that of the powder. Furthermore, β-form crystals did not deliquesce at RH of 64%, but the powder deliquesced at this humidity.

4. Heat Stability

To evaluate the heat stability of β-form crystals of deoxyspergualin hydrochloride in comparison with that of the powder, samples were stored at 50° C. for 6 days, and analyzed by HPLC to measure the amount of undecomposed substance. The results are shown in Table 6.

TABLE 6

| | Comparison of heat stability | |
|---|---|---|
| | Powder | β-form crystals |
| Amount (%) | 89.8 | 100.6 |

Note:
Amount (%) = $\frac{\text{Amount after storage}}{\text{Initial amount}} \times 100$ As apparent from Table 6, the β-form crystals shows remarkable improvement in heat stability.

The invention will be further explained by means of the following Examples. It should be understood however that the invention is not limited to these examples.

EXAMPLE 1

Powder of deoxyspergualin hydrochloride (500 mg) was left standing at 25° C. and RH of 52% for 11 days to allow crystallization. The crystals (506 mg) obtained showed the X-ray diffraction pattern typical of α-form crystals depicted in FIG. 1.

EXAMPLE 2

A lyophilized powder of deoxyspergualin hydrochloride (500 mg) was left standing at 25° C. and RH of 43% for 11 days to yield α-form crystals (510 mg).

EXAMPLE 3

A lyophilized powder of deoxyspergualin hydrochloride (500 mg) was left standing at 25° C. and RH of 31% for 11 days to yield α-form crystals (509 mg).

EXAMPLE 4

An aqueous solution (100 ml) of 40 g of deoxyspergualin hydrochloride was concentrated under reduced pressure to yield a syrupy residue (46 g). To the residue was added 20 mg of α-form crystals, and the mixture was stirred at a RH of 15% at the room temperature. After being stirred for 2 hr, the solidified residue was left standing in a silica gel desiccator for 3 days to yield α-form crystals (42 g).

EXAMPLE 5

To a vial containing 100 mg of powder of deoxyspergualin hydrochloride was added 0.5 ml of 95% (v/v) aqueous ethanol, and the solution was left standing at 5° C. for 3 days. The crystals formed in the solvent were collected by filtration under reduced pressure, and dried under reduced pressure to yield 55 mg of β-form crystals. X-ray diffraction pattern of the crystals obtained showed the X-ray diffraction pattern typical of β-form crystals depicted in FIG. 3.

EXAMPLE 6

An aqueous solution (100 ml) containing 20 g of deoxyspergualin hydrochloride was concentrated under reduced pressure to yield 24 g of a syrupy residue. To the residue was added 75 ml of ethanol, and 20 mg of β-form crystals was seeded. The mixture was left standing at 5° C. for 9 days. The crystals were collected as in Example 5 and dried, giving β-form crystals (16 g).

EXAMPLE 7

An aqueous solution (500 ml) of deoxyspergualin hydrochloride (150 g) was concentrated under reduced pressure to obtain a syrupy residue (175 g). To the residue was added 1 liter of ethanol, and the solution was stirred at 5° C. for 2 days. The crystals formed were collected by centrifugal filtration, and dried under reduced pressure, giving 129 g of β-form crystals.

EXAMPLE 8

An aqueous solution (4 liters) of deoxyspergualin hydrochloride (950 g) was concentrated under reduced pressure to obtain a syrupy residue (1120 g). To the residue was added 1.5 liter of ethanol, and the suspension was transferred to a vessel (10 liters volume) for crystallization. To the mixture were added 6.5 liters of ethanol and 2 g of β-form crystals with stirring, and stirring was continued at 15° C. for 4 days. The crystals were collected by centrifugal filtration, and dried under reduced pressure, yielding 880 g of β-form crystals.

The crystalline deoxyspergualin hydrochloride of the present invention is novel and possesses improved hygroscopicity and heat stability, which results in easier handling of deoxyspergualin during formulation and storage.

EXPERIMENTS

The procedures of EXAMPLE 6 of Umeda et al U.S. Pat. No. 4,603,015 have been repeated except that the scale has been somewhat reduced.

SYNTHESIS

N-[4-(3-aminopropyl)aminobutyl]-2-(7-guanidinoheptanamido)-2-hydroxyethanamide

A mixture of 10.0 g (45.0 m moles) of 7-guanidinoheptanamide hydrochloride, 13.1 g (45.0 moles) of N-[4-(3-aminopropyl)aminobutyl]-2,2-dihydroxyethanamide dihydrochloride, and 3.2 g (15 m moles) of citric acid in water (100 ml) was evaporated to dryness to give a syrup which contained 1.0 g of water. The resulting syrup was heated at 60° C. for 8 hours.

PURIFICATION

After completion of the above reaction, 100 ml of water was added to the reaction mixture, then passed through a column (35 mm inner diameter) packed with 500 ml of CM-Sephadex ® C-25 (Na-type), and fractionated by the gradient elution with 5 liters of water and 5 liters of 0.8M aqueous sodium chloride solution. The fractions containing the desired product were combined, then concentrated, and extracted three times with 20 ml of methanol. The methanol layer was passed through a column packed with 500 ml of Sephadex ® LH-20, and developed with methanol. The fractions containing the desired product were combined and evaporated to dryness, yielding 10.2 g (45.5 yield) of white powder of N-[4-(3-aminopropyl)aminobutyl]-2-(7-guanidinoheptanamido)-2-hydroxyethanamide trihydrochloride (hereinafter referred to as "Powder A").

X-RAY DIFFRACTION PATTERN

Figure 5:
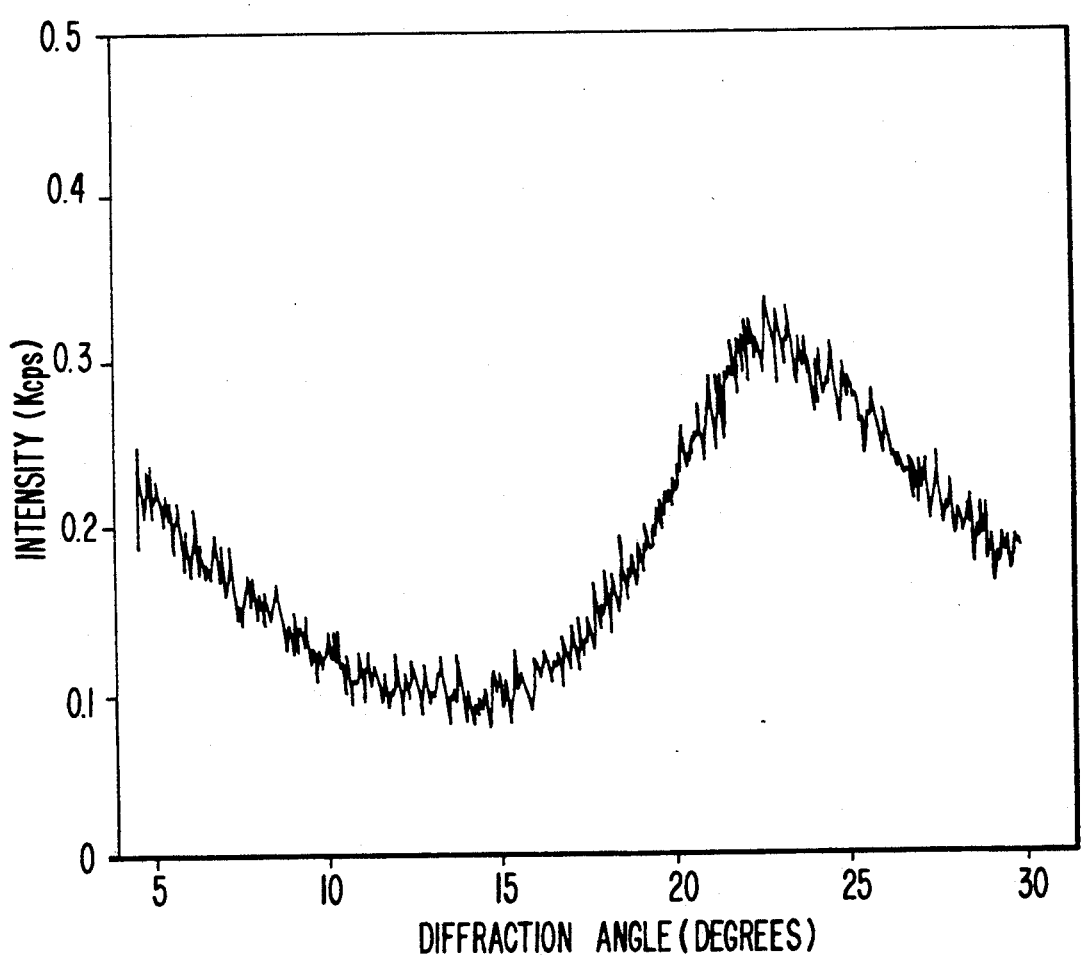

The Powder A was subjected to an X-ray diffraction pattern analysis. An X-ray diffraction apparatus (Shimadzu XD-3A) equipped with a Cu X-ray tube, graphite monochrometer and scintillation counter for detection was used. The X-ray diffraction pattern is shown in FIG. 5 (attached hereto) with the diffraction angle (degrees) on the abscissa and the intensity (Kcps) on the ordinate. As apparent from FIG. 5 the white Powder A is amorphous and there is observed no crystallinity in contrast to the α-form crystals and β-form crystals.

HYGROSCOPICITY

The hygroscopicity each of the Powder A and α-form crystals and β-form crystals of the above-identified application was evaluated by measuring the change in weight after storage in various RH (%) for 24 hrs. The results are shown in the following Table 7.

TABLE 7

| | Increase in weight (%) | | |
|---|---|---|---|
| RH(%) | Powder A | α-form crystals | β-form crystals |
| 31 | 5.0 | −0.6 | 1.2 |
| 43 | 6.3 | −0.4 | 2.1 |
| 52 | 7.4 | −0.1 | 3.0 |
| 64 | 13.2 | 15.2 | 6.1 |

HEAT STABILITY

To evaluate the heat stability of the Powder A in comparison with those of α-form crystals and β-form crystals of the above-identified application, samples were stored at 50° C. for 6 days and then analyzed by HPLC to measure the amount of undecomposed substance. The results are shown in the following Table 8.

TABLE 8

| | Powder A | α-form crystals | β-form crystals |
|---|---|---|---|
| Amount (%) | 59.7 | 100.1 | 100.2 |

Note:
Amount (%) = $\frac{\text{Amount after storage}}{\text{Initial amount}} \times 100$

OBSERVATIONS

The product obtained by the synthesis and subsequent purification disclosed in EXAMPLE 6 of Umeda et al U.S. Pat. No. 4,603,015 was in the form of white powder and not crystalline. Its hygroscopicity is much higher and its thermal stability is much lower than the α-form crystals and β-form crystals disclosed in the above-identified application.

Furthermore, the present invention relates to a novel suppository containing 15-deoxyspergualin trihydrochloride β-form crystals usable as an anticancer agent or an immunosuppressor.

As a result of the various researches, the present inventors have found that a powder or an aqueous syrup of known 15-deoxyspergualin trihydrochloride (hereinafter refers to as "15-deoxyspergualin hydrochloride") is crystallized in the presence of a mixture of water and a water miscible solvent, and the resulting crystals (hereinafter refers to as "β-form crystals") are mixed with a lipophilic base which is solid at an ambient temperature to give a suppository, which gives high concentration of 15-deoxyspergualin in blood when administered and has a good stability for storage, and have accomplished the present invention.

Thus, the present invention relates to a 15-deoxyspergualin suppository comprising β-form crystals of 15-deoxyspergualin hydrochloride and a lipophilic base which is solid at an ambient temperature.

For formulation of the suppository of the present invention, one or a mixture of two or more lipophilic bases, each of which is solid at normal ambient temperature, are melted by heating, and 15-deoxyspergualin hydrochloride β-form crystals are added thereto, and homogenized. The mixture is filled into suppository containers or gelatin capsule shells and cooled to give suppositories.

15-deoxyspergualin hydrochloride β-form crystals are used in an amount of about 1–40% (herein and hereinafter means "% by weight"), preferably 3–25%, more preferably 10–20% based on the total weight of the preparation. The amount of base is 60–99%, preferably 75–97%, and more preferably 80–90%. For various purposes, other additives can be added to the preparation of the present invention. The amount of the additives is 0–0.3 part (herein and hereinafter means "part by weight") relative to 1 part of the mixture of 15-deoxyspergualin hydrochloride β-form crystals and the base. The amount of the base is not less than 3 parts, preferably 4–100 parts relative to 1 part of the β-form crystals.

The lipophilic base which is solid at an ambient temperature used in the present invention includes medium chain fatty acid triglycerides which are solid at an ambient temperature (e.g. capric acid triglyceride); and oil and fat suppository bases (e.g. cacao butter, laurine butter, cinnamon butter, hydrogenated oil, semi-synthetic oil and fats, and the like). They can be used alone or in combination of two or more of them.

Examples of the lipophilic base which is solid at a normal ambient temperature are triglycerides of $C_8$–$C_{18}$ saturated fatty acids, which preferably contain at least 50% of $C_8$–$C_{14}$ saturated fatty acids. The fatty acids which constitute the triglycerides preferably contain one or more members selected from the group consisting of $C_8$, $C_{10}$, $C_{12}$ and $C_{14}$ saturated fatty acids.

The fatty acids attached to glycerin preferably contain about 32—about 60%, preferably about 44—about 57% of a $C_{12}$ saturated fatty acid; about 12—about 25%, preferably about 17—about 23% of a $C_{14}$ saturated fatty acid; about 9—about 20%, preferably about 10—about 14% of a $C_{16}$ saturated fatty acid; about 9—about 32%, preferably about 10—about 22% of a $C_{18}$ saturated fatty acid; and about 0—about 4%, preferably about 0—about 2% of other fatty-acid based on the total weight of the fatty acids.

The suppository of the present invention may be a capsule for rectal use which is prepared by molding suppositories by use of gelatin capsule shells and filling a mixture of the medicine (solution or solid) and the base therein.

Besides the above components (15-deoxyspergualin and the suppository base), additives may be added to the suppository of the present invention, for example, viscosity modifying agents such as microcrystalline wax and microcrystalline cellulose; substances to reduce rectal irritation such as fractionated coconut oils; a little amount of lecithin for prevention of blooming of fats. The amount of these additives is 0-30% based on the total weight of the drug and the suppositiory base.

The present invention is illustrated by the following examples. 15-deoxyspergualin refers to as "DSG" hereinafter.

EXAMPLE 9

Formulation

| β-form of DSG | 1 g |
|---|---|
| Pharmasol H-15* | 26 g |

*Nippon Oil & Fats Co., Ltd.

The above components are for 20 suppositories.

Pharmasol H-15 (proportion of fatty acids: about 54% of a $C_{12}$ fatty acid; about 22% of a $C_{14}$ fatty acid; about 12% of a $C_{16}$ fatty acid; and about 12% of a $C_{18}$ fatty acid) in a beaker was melted by heating on a water bath. After stopping heating, 1 g of DSG was added at 40° C. to the solution with stirring and homogenized with enough mixing. The mixture was poured into suppository molds (suppository containers), cooled at room temperature then solidified by cooling in a refrigerator to give suppositories.

EXAMPLE 10

Formulation

| β-form of DSG | 1 g |
|---|---|
| Panacete 1000* | 26 g |

*triglyceride of capric acid (made by Nippon Oil & Fats Co., Ltd.).

In a similar manner to that of Example 9, suppositories were obtaied.

EXAMPLE 11

Formulation

| β-form of DSG | 5 g |
|---|---|
| Pharmasol H-15 | 35 g |

The above components are for 20 suppositories.

In a similar manner to that of Example 9, suppositories were obtained.

REFERENCE EXAMPLE 1

A powder of DSG was dissolved in water to give a solution of 10 mg of DSG/ml.

REFERENCE EXAMPLE 2

50 mg of a powder of DSG and 50 mg of Panacete 1000 were mixed and filled into No. 3 capsules (the Pharmacopoeia of Japan).

REFERENCE EXAMPLE 3

Formulation

| Powder of DSG | 1 g |
|---|---|
| Macrogol* 1500 (trade name) | 18 g |
| Macrogol* 4000 (trade name) | 8 g |

(*Trade Name: polyethleneglycol)

Macrogol 1500 and Macrogol 4000 were taken into a beaker, and melted on a warmed water bath. DSG was added little by little to the solution with stirring and homogenized with enough mixing. The mixture was filled into suppository molds, solidified by cooling to give suppositories.

TEST EXAMPLE 1

(1) Test Method

Suppositories prepared in Examples 9 and 10 were each rectally administered to male beagles weighing 9.0-11.0 kg (3 animals were used for each group). As control, 5 ml of a solution obtained in Reference Example 1 was orally or rectally administered, a capsule obtained in Reference Example 2 was orally administered, and the suppository of Reference Example 3 was rectally administered. In all cases, doses of DSG were 5 mg/kg. Animals were fasted from the day before the beginning of the test to the conclusion of the test. Each about 5 mg of blood samples was collected into a heparin treated sylinge at 0.5, 1, 2, 4 and 8 hours after administration, and centrifuged to separate the serum.

To 1 ml of the serum was added 1 μg of N-[4-(3-aminopropyl)-aminobutyl]-2-(7-guanidinooctanamido)-2-hydroxyethanamide as an internal standard, and the mixture was diluted with 5 ml of distilled water and injected into CM-Sephadex C-25 column [$Na^+$ type (Pharmacia Fine Chemical Co.) 5 cm×0.5 cm φ]. The column was washed with 10 ml of 0.3M aqueous sodium chloride solution, and then DSG and the internal standard were eluted with 10 ml of 0.5M aqueous sodium chloride solution. After desalting by using Sep-Pak $C_{18}$ cartridge, the mixture was eluted with methanol, and the solvent was evaporated under reduced pressure.

The residue was dissolved in 250 μl of distilled water, and 100 μl of the solution was injected into high performance liquid chromatography (HPLC), treated with o-phthalaldehyde (OPA) to give its derivative (so-called postcolumn derivatization), which was determined by HPLC with fluorescence detector.

HPLC: Shimadzu liquid chromatography apparatus
Column: Cosmosil $5C_{18}P$ (15 cm×4.6 mmφ)
Column temperature: 25° C.
Detection wavelength: excitation wavelength 335 nm, emission wavelength 435 nm.
Mobile phase: 5 mM sodium heptanesulfonate was dissolved in 10 mM phosphate buffer (pH 3.0)—acetonitrile (80:20)
Flow rate: mobile phase 1.0 ml/min; OPA reagent 0.5 ml/min.

(2) Test Results

TABLE 9

| Sample | Phamacokinetic Parameter | |
|---|---|---|
| | $C_{max}$ (μg/ml) | AUC 0-8 hr (μg/hr/ml) |
| Example 9 | 1.126 | 2.310 |
| Example 10 | 0.890 | 1.396 |
| Control 1 (Oral administration of the aqueous solution) | 0.318 | 0.775 |
| Control 1 (Rectal administration of the aqueous solution) | 0.126 | 0.144 |
| Control 2 (Oral administration of the capsule) | 0.225 | 0.541 |
| Control 3 | 0.217 | 0.320 |

TABLE 9-continued

| | Phamacokinetic Parameter | |
|---|---|---|
| Sample | $C_{max}$ (μg/ml) | AUC 0-8 hr (μg/hr/ml) |
| (Rectal administration) | | |

$C_{max}$: The maximum plasma concentration
AUC 0-8 hr: Area under the plasma concentration - time curve (0-8 hours)

TEST EXAMPLE 2

Stability (Severe Test)

Test Method

To 50 mg of exactly weighed β-form crystals of DSG (or a lyophillized powder of DSG) in a hermetic vial was added 1.25 g of Witepsol ® (proportion of fatty acids: about 54% of a $C_{12}$ fatty acid; about 22% of a $C_{14}$ fatty acid; about 12% of a $C_{16}$ fatty acid; about 12% of a $C_{18}$ fatty acid) which was melted by heating on a water bath, and then the mixture was thoroughly mixed. After being tightly closed, the mixture was kept at 50° C. for 2 weeks or at 45° C. for 4 weeks.

The amount of DSG extracted from the base was measured according to a HPLC technique.

TABLE 10

| Remaining ratio of DSG in the suppository base | | |
|---|---|---|
| | Remaining ratio of DSG | |
| Sample | 35° C., 4 w | 50° C., 2 w |
| β-form crystals of DSG | 98.7% | 101.8% |
| Lyophillized powder of DSG | 95.8% | 76.3% |

TEST EXAMPLE 3

Hygroscopicity Test

Test Method

| Sample | |
|---|---|
| 1. β-form crystals of DSG | 2 g |
| Pharmasol H-15 | 26 g |
| 2. Lyophillized powder of DSG | 2 g |
| Pharmasol H-15 | 26 g |

The above components are for 20 suppositories.

26 g of Pharmasol H-15 in a beaker was melted by heating on a water bath. After stopping heating, 2 g of β-form crystals of DSG (a lyophillized powder of DSG) was added to the solution at 40° C. with stirring, homogenized with enough mixing, filled into suppository molds, cooled at room temperature and solidified by cooling in a refrigerator to give suppositories.

The above suppositories were stored at 25° C. at 75% RH, and the increase ratio of weight of the sample was measured.

Test Results

TABLE 11

| Hygroscopicity of suppositories | | | | |
|---|---|---|---|---|
| | Increase ratio of weight (%) | | | |
| Sample | 1 w | 2 w | 3 w | 4 w |
| β-form crystals of DSG | 2.0 | 2.7 | 3.6 | 4.4 |
| Lyophillized powder of DSG | 4.8 | 6.2 | 7.4 | 8.4 |

As shown in Table 9, the plasma concentration of DSG obtained by administration of the suppository of the present invention is higher than the concentrations obtained by the oral administration of DSG, by the rectal administration using the aqueous solution of DSG, and by the rectal administration of the suppository of DSG using a hydrophilic base (Macrogol). Particularly, the plasma concentration of DSG obtained by administered the suppository using the lipophilic base in Example 9 is about 3.5 times at $C_{max}$ higher and about 3 times at AUC (0-8 hr) higher than that obtained by administered Control 1 which is highest in the control group.

As shown in Tables 10 and 11, the suppository containing β-form crystals of DSG has higher stability of DSG and lower hygroscopicity of the suppository than the suppository containing a lyophillized powder of DSG.

It is apparent that, according to the invention, there is provided a 15-deoxyspergualin suppository which can be obtained high plasma concentration of 15-deoxyspergualin when administered and has good stability for storage.

What we claim is:

1. Crystalline deoxyspergualin trihydrochloride.

2. Crystalline deoxyspergualin trihydrochloride as in claim 1, wherein it is in the form of α-form crystals or β-form crystals.

3. α-form crystals of deoxyspergualin trihydrochloride having an X-ray powder diffraction pattern substantially as follows:

| d (Å) | I/I₁ | d (Å) | I/I₁ |
|---|---|---|---|
| 11.78 | 0.46 | 4.04 | 0.76 |
| 10.64 | 0.53 | 3.90 | 0.91 |
| 7.49 | 0.34 | 3.78 | 0.76 |
| 5.03 | 0.36 | 3.50 | 1.00 |
| 4.72 | 0.51 | 3.39 | 0.95 |
| 4.39 | 0.84 | 3.12 | 0.64. |

4. β-form crystals of deoxyspergualin trihydrochloride having an X-ray powder diffraction pattern substantially as follows:

| d (Å) | I/I₁ | d (Å) | I/I₁ |
|---|---|---|---|
| 15.77 | 0.32 | 4.14 | 0.70 |
| 10.91 | 0.42 | 3.66 | 1.00 |
| 4.88 | 0.39 | 3.31 | 0.52 |
| 4.67 | 0.53 | 3.21 | 0.52. |

5. A process for the preparation of β-form crystals of deoxyspergualin trihydrochloride, which comprises crystallizing powder or water-suspension syrup of deoxyspergualin trihydrochloride in the presence of ethanol, the concentration of the ethanol in the crystallization system being 85 to 99.5% (v/v).

* * * * *